United States Patent [19]
Lontrade et al.

[11] Patent Number: 5,310,085
[45] Date of Patent: May 10, 1994

[54] METHOD AND PACKAGING FOR PRESERVING AND DISPENSING PORTIONS OF A STERILE LIQUID

[75] Inventors: Jean-Pierre Lontrade; Henri Chibret, both of Clermont-Ferrand, France

[73] Assignee: Transphyto SA, Clermont-Ferrand, France

[21] Appl. No.: 946,355

[22] PCT Filed: Apr. 10, 1991

[86] PCT No.: PCT/FR91/00291
§ 371 Date: Oct. 27, 1992
§ 102(e) Date: Oct. 27, 1992

[87] PCT Pub. No.: WO91/16868
PCT Pub. Date: Nov. 14, 1991

[30] Foreign Application Priority Data
Apr. 27, 1990 [FR] France ............... 90 05369

[51] Int. Cl.$^5$ ............................................. B67B 7/00
[52] U.S. Cl. ........................................ 222/1; 222/179.5; 222/420; 222/189
[58] Field of Search ............... 222/189, 212, 215, 92, 222/420, 179.5, 1

[56] References Cited
U.S. PATENT DOCUMENTS

| | | | |
|---|---|---|---|
| 2,363,474 | 11/1944 | Schlesinger | 222/179.5 |
| 3,248,017 | 4/1966 | Allen | 222/420 X |
| 4,248,361 | 2/1981 | Moyle | 222/179.5 |
| 4,463,880 | 8/1984 | Kramer et al. | 222/420 X |
| 4,950,237 | 8/1990 | Henault et al. | 222/420 X |
| 5,105,993 | 4/1992 | La Haye et al. | 222/420 X |

Primary Examiner—Gregory L. Huson
Attorney, Agent, or Firm—Millen, White, Zelano & Branigan

[57] ABSTRACT

Liquid is enclosed in a resiliently deformable container, the neck of which has a microfiltering membrane which is permeable to the liquid but impermeable to air when wet. Since the container resiliently recovers its shape after it is deformed, the liquid remaining in contact with the outside of the membrane after use is sucked back in and the membrane is kept moist until the next time the container is used.

14 Claims, 3 Drawing Sheets

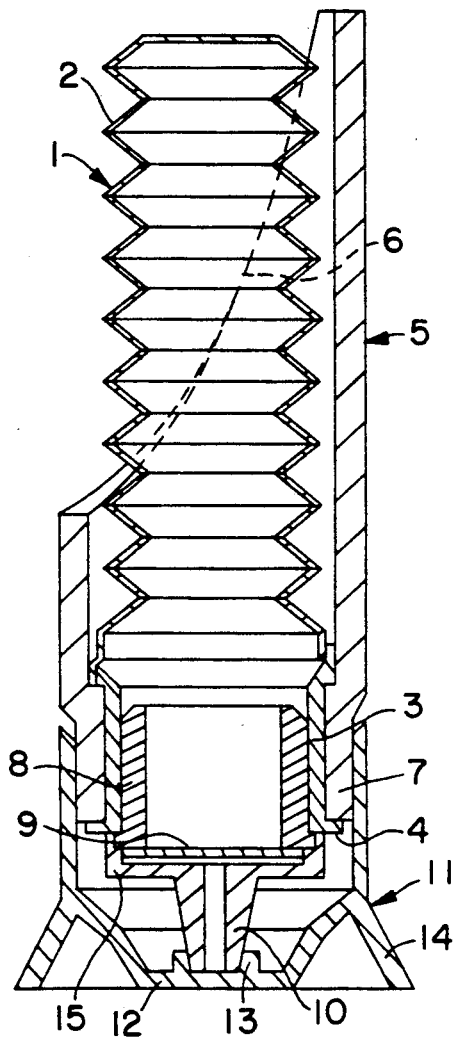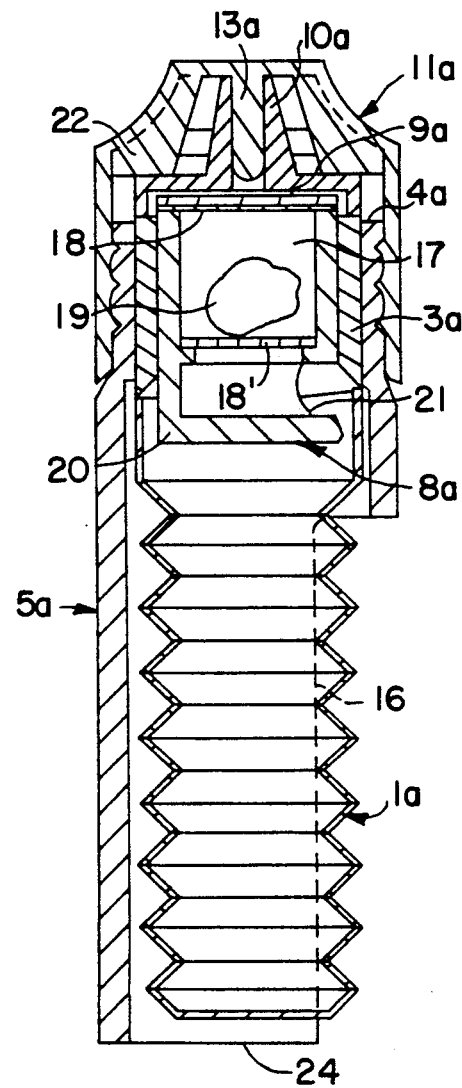
FIG. 1
FIG. 2

METHOD AND PACKAGING FOR PRESERVING AND DISPENSING PORTIONS OF A STERILE LIQUID

SUMMARY OF THE INVENTION

The present invention relates to the packaging industry and more particularly to the packaging of sterile substances to be dispensed in portions such as eye lotions.

Substances of this type have been packaged in rigid containers with separate droppers, then in elastically deformable containers with a dropper nozzle, always with the risk of contamination of the unused liquid which is kept for subsequent use within the container after contact with the atmosphere. It has subsequently been proposed to employ containers in which sterility of the contents is preserved by a sterilizing filter interposed within the opening of the container, which can consist of a ceramic component but which consists in most cases of a microporous membrane of plastic material as described in particular in French patent No. 2,422,569. However, there inevitably remains a small quantity of liquid outside the membrane after a delivery. This liquid thus fails to escape external contamination. A subsequent delivery of liquid which has been kept in a sterile condition is then contaminated by said liquid which has remained outside the membrane.

Sterilizing filters constituted by microporous membranes have the property of becoming impermeable to air in the wet state except under high pressure. This property has so far been considered as a drawback. French patent 2,422,569 proposes to form in the membrane a zone which is impermeable to liquids but permeable to air, for example by local waterproofing with silicone in the case of aqueous liquid. This enables an elastically deformable container to suck-in air in order to compensate for the volume of liquid delivered and thus recover its initial shape. But, the differential pressure on each side of the membrane which permits suction of air is lower than the pressure which would permit suction of the liquid. As a result, the liquid which has passed through the membrane cannot be recovered and kept in a sterile condition.

If a membrane having zones which are permeable to air or to liquids is not employed, French patent 2,422,569 mentions the possibility of employing non-elastic deformable containers, for example of thin aluminum, having a volume which decreases in proportion to the number of deliveries performed. But, containers of this type are incapable of sucking-in the liquid which has passed through the membrane and thus remains in contact therewith after a delivery.

The invention, on the contrary, takes advantage of this alleged drawback in order to avoid any loss and contamination of the liquid which remains in contact with a microporous membrane after a delivery.

The object is achieved by keeping the membrane moistened by the liquid between successive deliveries and therefore impermeable to air while continuously subjecting it to a differential pressure of suction of the liquid, the value of which is not sufficient to permit forcible suction of air through the wet membrane.

The minimum differential pressure which permits air to pass through a wet microporous membrane is commonly determined by the so-called "bubble point" test whereby one face of the wet membrane is subjected to an increasing air pressure. The specific value retained for the "bubble point" is the differential pressure which causes the appearance of a continuous flow of bubbles downstream of the membrane. The bubble-point values specific to each type of membrane are usually provided by their manufacturers.

The invention thus relates to a method for dispensing portions of sterile liquid enclosed in a container under the control of a microfiltering membrane, which is permeable to the liquid but impermeable to air when wet and which is interposed within the neck, without contaminating the liquid remaining between deliveries. The method is distinguished by the fact that the membrane is moistened with liquid from within the interior of the container prior to the first delivery; the desired quantity of liquid is delivered through the membrane by exerting pressure on the liquid within the container; the liquid remaining in contact with the outer face of the membrane is selectively sucked into the container after delivery without any suction of air; and the membrane is kept moistened with liquid between successive deliveries.

In accordance with this method, the liquid can be stored within a container which is elastically deformable by hand and which produces between the faces of the membrane, as a result of shape recovery after deformation, a differential pressure lower in value than that of the bubble point of the membrane but at least equal to the value which is necessary for suction of the liquid through the membrane.

By way of an alternative, a volume of gas which is inert with respect to the liquid can be enclosed in the container together with the liquid. Compression of said volume of gas by manual deformation of the container permits delivery of practically the entire quantity of liquid through the membrane.

In fact, conventional containers are not capable of complete elastic deformation, especially at the neck, and it is impossible in these cases to discharge the entire quantity of the liquid simply by applying pressure on the deformable portion except by transmitting to the liquid the pressure exerted on the deformable wall by means of a sufficient quantity of air or other gas enclosed within the container together with the liquid.

The invention also concerns a package for carrying out the method in accordance with the invention and dispensing sterile liquid, especially liquid which is sensitive to contact with air, including a container having a wall which is elastically deformable by manual compression, the delivery opening of which is controlled by a microfiltering membrane which is permeable to the liquid but impermeable to air and in the wet state. The package is distinguished by the fact that the force of elastic shape recovery of the container wall after manual deformation produces between the faces of the membrane a differential pressure lower than the differential pressure of the bubble point which permits the flow of air through the wet membrane. As result, after discharge of liquid to the exterior through the membrane under the action of pressure exerted externally on the container, the liquid remaining in contact with the outer face of the membrane, when external pressure is no longer exerted, returns selectively into the container through the membrane by suction under the action of the negative pressure produced within container by the shape recovery of its wall without any possibility of concomitant suction of external air.

In a package of this type, the differential pressure of the bubble point of the membrane is usually about 4 bar while the resilient shape recovery of the container after deformation is about 0.003 bar.

In an advantageous embodiment, the membrane is covered externally by a dispenser head which guards the outer face of the membrane against any deformation which would be liable to impair its integrity while permitting discharge of liquid which has passed through the membrane towards a capillary dispenser nozzle. The maximum total volume of liquid between the outer face of the membrane and the tip of the nozzle is approximately 1 to 3 drops.

A package in accordance with the invention can advantageously include an end cap which serves to seal the liquid dispenser head and constitutes a base for storage of the container in an inverted position, thus maintaining the liquid of the container in permanent contact with the membrane.

In a preferred embodiment of the package in accordance with the invention, the package is advantageously provided with means designed to impose storage in the inverted position so as to ensure that the membrane is kept in the wet state even during long periods of storage when the end cap for closing the dispenser head is not fitted in position.

The above-mentioned means advantageously provide the package with instability in a position in which the dispenser head is directed upwards and are preferably associated with bearing means adapted to endow the package with stability in the inverted position.

Providing said means makes it possible in particular to elude a problem of the membrane drying-up by evaporation, especially if the user forgets to re-close the dispenser head with the closure end cap over a long storage period. In other forms of construction, this can also avoid the need to provide a closure end cap.

In accordance with a particularly advantageous feature of the package according to the invention, said container having an elastically deformable wall has a rear surface constituting an unstable bearing surface which serves to impose storage in the inverted position.

The package in accordance with the invention advantageously has a rigid sheath for protecting said container which has an elastically deformable wall. The sheath is preferably open at the rear end so that said container projects beyond the sheath in the position of rest, thus making it possible to maintain instability of the package in any position other than the inverted position.

In an alternative embodiment of the package in accordance with the invention, the rigid sheath is cutaway from the rear end thereof in order to ensure that the sheath does not afford a bearing surface for storage of the package, for example, by being widely cut so as to form a bevelled end portion. In this case, the sheath itself constitutes the means designed to impose storage in the inverted position.

By way of an alternative, the package can have a tube which extends downwards to the bottom of the container and has an external goosenecked extension terminating in a dispenser head which contains the membrane.

In another alternative embodiment, the package has a hand pump, without any mechanical valve, incorporated in a shrinkable container which discharges the liquid of the container through a membrane which is permeable only to the liquid, forming a selective non-return valve against the action of a resilient restoring force calibrated at a force which is lower than that of the bubble point of the membrane.

BRIEF DESCRIPTION OF THE DRAWINGS

A better understanding of the invention will be gained from a study of the detailed description of the accompanying drawings which illustrate a number of embodiments chosen solely by way of example among the numerous forms of execution, adaptation, and variants of the invention within the capacity of any one versed in the art.

In these drawings:

FIG. 1 is a schematic view in elevation and in axial cross-section of a first embodiment of a package in accordance with the invention;

FIG. 2 is a view which is similar to that of FIG. 1 and shows a second embodiment;

In these figures, the corresponding elements are designated by the same reference numerals which may be followed by an index. The respective dimensions and proportions of these elements may not be observed for the sake of enhanced legibility of the drawings.

DETAILED DESCRIPTION

Figure 3:
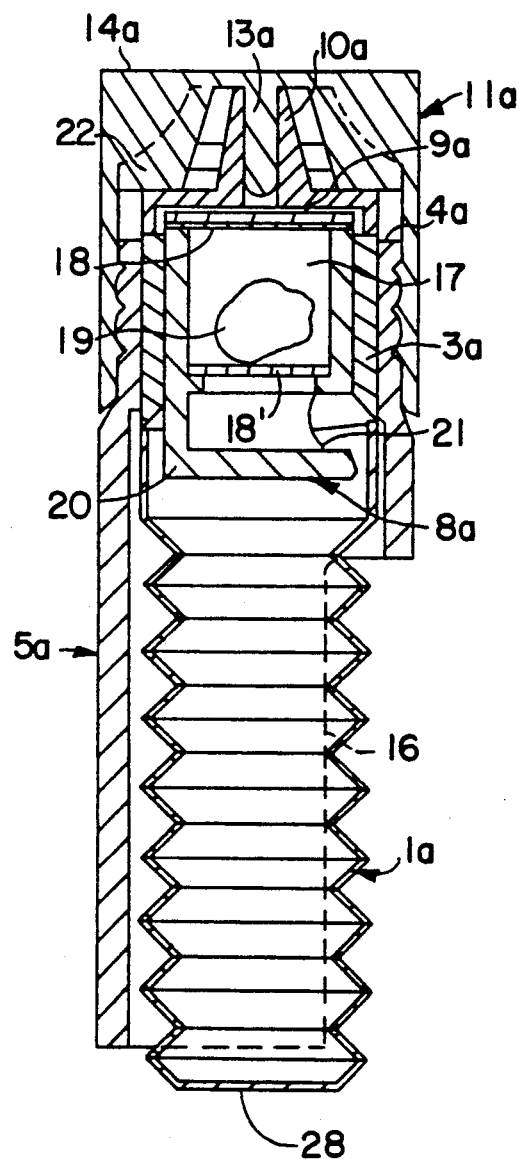
FIG. 3 is an alternative embodiment of the package shown in FIG. 2.

The package for dispensing sterile liquid as illustrated in FIG. 1 mainly comprises a container 1 of blown plastic and of cylindrical shape, the rear portion 2 of which is pleated transversely to the axis in the same manner as an accordion. The front portion 3 of container is in the form of a cylinder of revolution and terminates in an annular flange 4 which surrounds the neck.

The container 1 is partly surrounded by an open sheath 5, the rear portion 6 of which is widely cut away so as to form a bevelled end portion, thus providing free access to the pleated portion 2 of the container. The front portion 7 of the sheath is a cylinder of revolution and receives the front portion 3 of the container in a tight fit, the annular flange 4 of said front portion 3 being attached by bonding, heat welding, ultrasonic welding or friction welding to the end face of the top edge of the sheath 5.

An open tubular plug 8 is inserted in a fluid-tight fit within the front portion 3 of the container. The external opening of said plug is closed by a microfiltering membrane 9 which is sealed by bonding, heat welding or ultrasonic welding of its periphery to the end face of the opening of the plug 8.

A dropper nozzle 10 is snap-fastened in fluid-tight manner on the lateral edge of the opening of the plug 8 and the periphery of its base is applied against the annular flange 4 of the container 1, thus leaving a small space between its flat bottom 15 and the membrane 9 for the flow of liquid.

A detachable tubular blind end cap 11 is inserted in an easy fit on the cylindrical top portion 7 of the sheath 5. Its base 12 is provided internally with an annular protuberance 14 which engages in a fluid-tight fit over the open end of the dropper nozzle 10. Externally, the base 12 is extended and surrounded by a frusto-conical flare 13 which serves as a base for placing the package in an inverted position, as shown in FIG. 1, on a table or other flat surface whereas the bevelled base of the sheath 5 makes it impossible to place the package vertically in the other direction since the bearing surface offered by the free end of the sheath on a flat surface of this type is too narrow. Thus, the membrane 9 remains wetted by the liquid of the container between periods of use.

For the purpose of packaging eye lotions, for example, it is advantageous to employ a hydrophilic microfiltering membrane of cellulose esters in the form of a circular disk approximately 1 cm in diameter having a mean pore size of 0.22 μm±0.02 and a bubble point of 3.87 bar, of the type sold under the trade name MF-Millipore type GS by the French company Millipore S.A. The membrane will be associated, for example, with a container, having a useful capacity of approximately 10 $cm^3$, of blown low-density polyethylene having an external diameter of approximately 15 mm. The container has about ten transverse bellows pleats having an internal diameter of approximately 12 mm and a mean wall thickness of approximately 0.5 mm. The partial vacuum produced by the shape recovery of said container after axial compression of the bellows pleats is approximately 0.002 to 0.004 bar.

The volume defined between the membrane and the opening of the dropper nozzle is from one to three drops, preferably 1 drop.

In the embodiments presented in FIGS. 2 and 3, there are again shown a number of elements similar to those of the first embodiment of FIG. 1: an accordion pleated container 1a surrounded by a sheath 5a covered by an end cap 11a. But, in this case, the cylindrical sheath is provided only with a longitudinal lateral slot 16 having a width such that the user can pass one finger through the slot. In the embodiment shown in FIG. 2, said sheath leaves at the open end of the sheath a semicircular seating 24 which is sufficient to support the package in an upright position on a table or other flat surface as shown in FIG. 2.

In the alternative embodiment shown in FIG. 3, the sheath 5a is so dimensioned in length that the rear end of the container 1a projects beyond the open end of the sheath and the rear end of the container 1a terminates in a rear surface 28 which constitutes an unstable bearing surface so that it is consequently necessary to store the package in the inverted position.

The membrane 9a is fixed at the end of a plug 8a which slides in fluid-tight manner within the cylindrical upper portion 3a of the container 1a. The plug constitutes a carriage with an internal housing 17 defined by two sieves 18, 18' between which there can be placed a substance 19 which is soluble in the liquid or by modifying or absorbing certain constituents. The base of the plug is closed by a partition 20 and a lateral opening 21 is located between the sieve 18' and the partition 20. The sieve 18 serves as a support for the membrane 9a over its entire useful surface and the dropper nozzle 10a is provided with splines which are in contact with the membrane and hold it in position without interfering with the flow of liquid.

Prior to initial use, the end cap 11a is screwed-down only to a partial extent and the plug 8a is only partially inserted in the neck of the container 1a in order to ensure that the bottom partition 20 isolates the housing 17 and its contents from the liquid within the container. The end cap 11a has an axial nipple 13a which is inserted in fluid-tight manner within the duct of the dropper nozzle 10a which isolates the membrane and the housing 17 from the exterior. The end cap also has internal radial fins 22 which bear on the outer face of the dropper nozzle in order to insert the latter as well as the plug 8a by screwing-down into the neck of the container for initial use until a position of abutting application against the annular end face 4a of the container is reached as shown in FIGS. 2 and 3, thus putting the interior of the plug into communication with the interior of the container.

During periods of storage of the package, the axial nipple 13a is engaged in fluid-tight manner within the duct or nozzle of the dropper 10a, thus ensuring that the membrane remains wet and is not liable to be dried by air coming in from the exterior.

A device of this type in which provision is made for a moving carriage forming a lock-chamber is described in European patent Application No. 89 40 29 16 4.

In the embodiment as illustrated in FIG. 3, the end cap 11a terminates in a bearing surface 14a for storage of the package in the inverted position.

Figure 4:
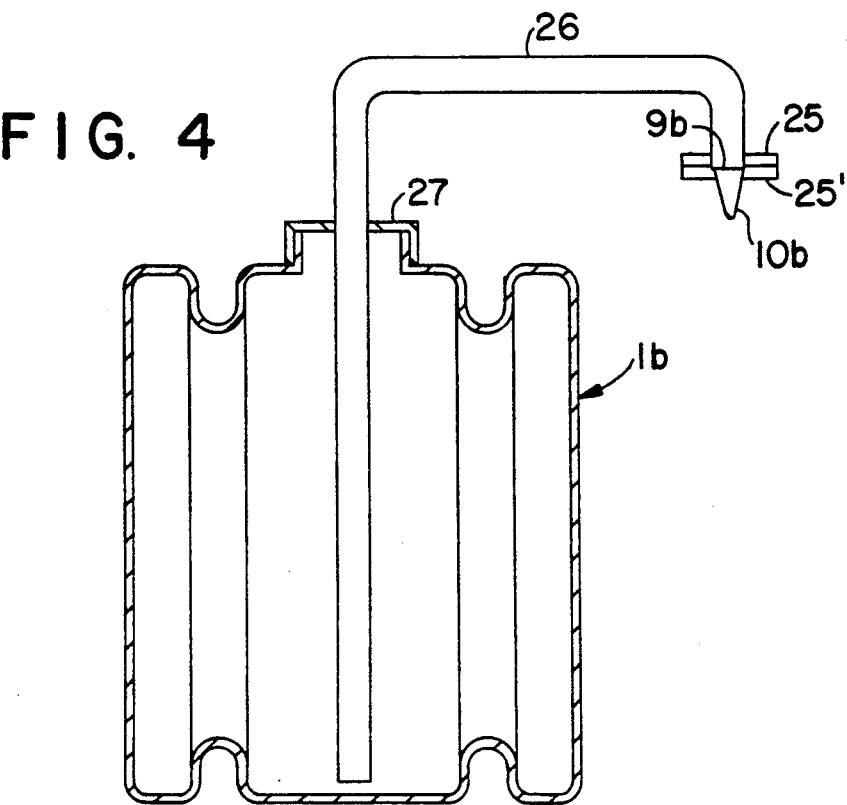
FIG. 4 is a view which is similar to the preceding and shows a fourth embodiment.
Figure 5:
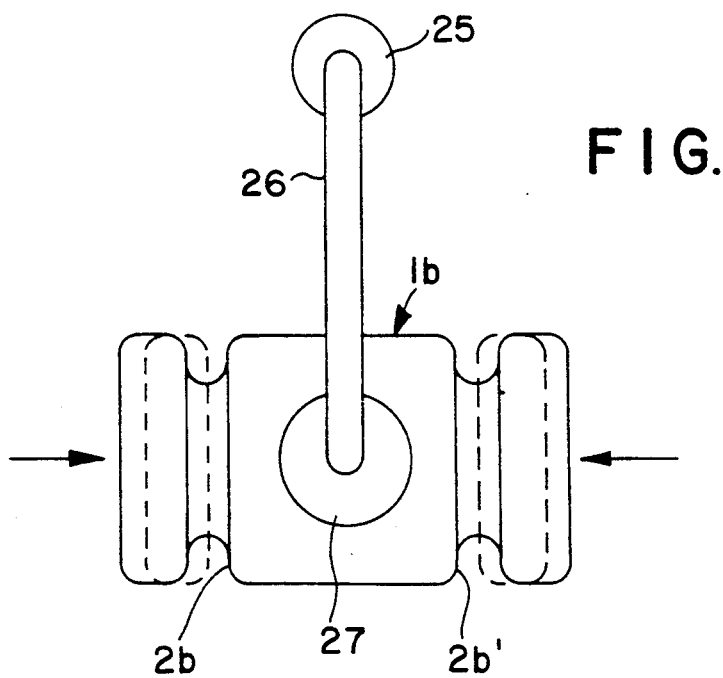
FIG. 5 is a schematic top view of a package which is identical with that of FIG. 4 but with a delivery tube displaced by 90°.

In the fourth embodiment illustrated in FIGS. 4 and 5, the membrane 9b is fixed between two assembled flange-plates 25, 25' derived in one case from a dropper head 10b and in the other case from the end of a tube 26, the opposite end of which extends axially downwards to the bottom of a container 1b having generally rectangular cross-section including two bellows pleats 2b, 2b' which extend symmetrically around the container in a direction parallel to its axis. The dashed lines indicate the deformation of the bellows pleats when the container is compressed laterally in the direction of the arrows of FIG. 5. The tube 26 passes in fluid-tight manner through a sealing disk 27 which tightly closes the neck of the container while being orientable if necessary in a direction parallel to the bellows pleats (FIG. 4) or transversely (FIG. 5) according to the user's requirements. Consideration can be given to the possibility of completely filling the containers with liquid but it appears more practical to fill them only to a partial extent, for example to two-thirds or to one-half in order to reserve a free space which will be filled with air or another gas and especially nitrogen, in a sterile state, in order to permit removal of practically the entire quantity of liquid. The membrane wetted by the liquid prevents outleakage of gas.

We claim:

1. A method for dispensing portions of sterile liquid enclosed in a container having a neck in which is positioned a microfiltering membrane for control of dispension of liquid, said membrane having an inner face and outer face and being permeable to the liquid but impermeable to air when said membrane is in a wet state, said method comprising:

moistening said membrane with liquid contained in said container prior to first delivery of a liquid portion, exerting pressure on liquid within said container to deliver a quantity of liquid through said membrane, after delivery of said quantity of liquid, selectively sucking liquid remaining in contact with said outer face of said membrane into said container without any suction of air, and keeping said membrane moistened with liquid between successive deliveries, whereby contamination of liquid remaining within said container between deliveries is prevented.

2. A method according to claim 1, wherein said container is elastically deformable by hand, whereby shape recovery after elastic deformation of said container produces, between the faces of the membrane, a differential pressure which is lower in value than the bubble point of said membrane.

3. A method according to claim 1, wherein a volume of gas, which is inert with respect to said liquid, is enclosed in said container together with said liquid and compression of said volume of gas by manual deformation of said container permits delivery of substantially the entire quantity of liquid through said membrane.

4. A device for dispensing sterile liquid comprising:
a container having a wall which is elastically deformable by manual compression, a delivery opening, and a microfiltering membrane which controls dispension of liquid through said delivery opening, said membrane having an inner face and outer face and being permeable to liquid but impermeable to air when said membrane is in a wet state,
wherein elastic shape recovery of said wall of said container after manual compression thereof produces between said faces of said membrane a differential pressure lower than the differential pressure of the bubble point which permits the flow of air through said membrane when wet, whereby, after expulsion of liquid through said membrane due to compression of said wall of said container, liquid remaining in contact with said outer face of said membrane is selectively returned into said container through said membrane by suction induced by the negative pressure produced within said container by said elastic shape recovery of said wall without any suction of external air;
said device further comprising means imposing storage of said container in an inverted position, thereby keeping said membrane moistened with liquid between successive deliveries.

5. A device according to claim 4, wherein said container has a rear surface which constitutes an unstable bearing surface.

6. A device according to claim 4, further comprising a rigid sheath for protecting said container, said sheath being cut away so as to permit access to said container in order to exert thereon a pressure which is suitable for discharging a portion of liquid.

7. A device according to claim 6, wherein said rigid sheath is open at the rear end thereof, with the result that said container projects beyond said rigid sheath in the rest position.

8. A device according to claim 6, wherein said rigid sheath is cut away in order to ensure that said rigid sheath does not afford a bearing surface for storage of said device.

9. A device according to claim 8, wherein said rigid sheath is cut to form a bevelled portion from the rear end thereof.

10. A device according to claim 9, wherein said membrane is covered externally by a dispenser head which guards said outer face of said membrane against any deformation which would be liable to impair its integrity while permitting discharge of liquid which as passed through said membrane towards a capillary dispenser nozzle, the total maximum volume of liquid between said outer face of said membrane and the top of said nozzle is 1 to 3 drops.

11. A device according to claim 10, further comprising an end cap which serves to seal said dispenser head and constitutes said means for storage of said container in an inverted position, thus maintaining liquid within said container in permanent contact with said membrane.

12. A device according to claim 4, wherein said device further comprises a tube which extends downwards to the bottom of said container and has an external goosenecked extension terminating in a dispenser head which contains said membrane.

13. A device according to claim 4, further comprising a hand pump, without any mechanical valve, incorporated in said container which discharges liquid within said container through a membrane which is permeable only to the liquid, thereby forming a selective non-return valve against the action of a resilient restoring force calibrated at a force which is lower than that of the bubble point of said membrane.

14. A device according to claim 4, wherein the differential pressure of the bubble point of said membrane is 4 bar while the differential pressure induced by elastic shape recovery of said container after deformation is 0.003 bar.

* * * * *